US008279440B2

(12) United States Patent
Frick et al.

(10) Patent No.: US 8,279,440 B2
(45) Date of Patent: Oct. 2, 2012

(54) HAND-HELD LIGHT MEASURING DEVICE

(75) Inventors: Beat Frick, Buchs (CH); Lido Feri, Baden (CH); Stefan Knechtle, Regensdorf (CH)

(73) Assignee: X-Rite Europe GmbH, Regensdorf (CH)

( * ) Notice: Subject to any disclaimer, the term of this patent is extended or adjusted under 35 U.S.C. 154(b) by 291 days.

(21) Appl. No.: 12/820,239

(22) Filed: Jun. 22, 2010

(65) Prior Publication Data

US 2010/0328656 A1    Dec. 30, 2010

(30) Foreign Application Priority Data

Jun. 24, 2009   (EP) .................................... 09163639

(51) Int. Cl.
*G01J 3/46*    (2006.01)

(52) U.S. Cl. ...................................................... 356/402

(58) Field of Classification Search ........... 356/402–425
See application file for complete search history.

(56) References Cited

U.S. PATENT DOCUMENTS

| | | | | |
|---|---|---|---|---|
| 2,728,265 A | * | 12/1955 | Stimson et al. | 356/45 |
| 2,917,969 A | * | 12/1959 | Stimm | 356/407 |
| 3,935,436 A | | 1/1976 | Holschlag et al. | |
| 4,455,090 A | | 6/1984 | Roberts | |
| 5,963,333 A | | 10/1999 | Walowit et al. | |

OTHER PUBLICATIONS

Zwinkels, J.C., Colour-Measuring Instruments and Their Calibration, Displays Devices, DEMPA Publications, Tokyo, Japan, Bd. 16, Nr. 4, pp. 163-171 (1996).
Handheld Color—Color-Guide Familay, BYK Gardner, Product Information, 2005, pp. 51-58, XP007910642 Internet: URL:http://www.analis.be/files/VprodFiles/270/BYKHandColorguideFam.pdf.
European Search Report dated Dec. 11, 2009.

* cited by examiner

*Primary Examiner* — Tara S Pajoohi Gomez
(74) *Attorney, Agent, or Firm* — McCarter & English, LLP

(57) ABSTRACT

A hand-held light measuring device includes a device housing (G) with a bottom face incorporating a measuring window (7) through which a measurement optical path extends so that a measurement object can be measured when the device housing (G) is positioned with its bottom face on the measurement object. The measuring device has an integrated, displaceably mounted white reference tile, which can be moved into the measurement optical path and moved back out of it again. The white reference tile is disposed in an end region of an oblong support plate (10) on its side directed towards the housing interior. The support plate (10) is mounted so that it can move backwards and forwards between a parked position and an operating position, and the support plate (10) terminates the device housing (G) at its bottom face and is recessed into the device housing (G) in the parked position, and the support plate (10) is lifted out from the bottom face of the device housing (G) and moved in the longitudinal direction and covers the measuring window (7) by means of the end region incorporating the white reference tile in the operating position. The kinematics of the support plate (10) and white reference tile are simple in design/operation and the support plate and white reference tile can be moved easily and comfortably.

10 Claims, 4 Drawing Sheets

HAND-HELD LIGHT MEASURING DEVICE

FIELD OF THE INVENTION

The invention relates to a hand-held light measuring device, in particular a hand-held color measuring device with a device housing.

BACKGROUND OF THE INVENTION

Numerous designs of hand-held light measuring devices are known. They are usually designed as densitometers or color measuring devices, and various measuring technologies are used. Many known hand-held light measuring devices are designed as spectral photometers and can therefore be used universally.

The known light measuring devices usually comprise an arrangement for illuminating the measurement object, a pick-up arrangement for detecting the measurement light reflected back from the measurement object, a photoelectric converter arrangement for converting the detected measurement light into corresponding electric signals and an electronic system for evaluating the electric signals and for controlling the operating sequences of the measuring device. The lighting arrangement may generate white light or may be designed for colored light. The converter arrangement may comprise a number of color filters or dispersive elements, e.g. a diffraction grating, for splitting the measurement light into different wavelength ranges. Photodiodes or CCD converter arrangements may be provided for the actual conversion into electric signals.

To measure a measurement object, the hand-held light measuring device is placed on the point of interest (measurement site) of the measurement object, and the measurement is taken through a measuring orifice disposed in the bottom face of the device housing.

What all of the known light measuring devices have in common is that they have to be calibrated from time to time. They are often equipped with an integrated white reference tile for this purpose, which can be introduced into the measurement optical path for calibration purposes. When using the device as normal for taking measurements, the white reference tile is disposed in a parked position outside of the measurement optical path. The white reference tile may be disposed on a support element which is able to slide or pivot in the device housing, for example. Also already known are light measuring devices where the measurement optical path is deflected onto a stationary mounted white reference tile using mirror elements which can be moved into it and moved back out of it again. Alternatively, the white reference tile may be provided as a separate component which takes the place of a measurement object for calibration purposes.

SUMMARY OF THE INVENTION

Against the background of this prior art, the objective of this invention is to propose a hand-held light measuring device which is better in terms of the construction and kinematics of its integrated white reference tile. In particular, no additional optical components are needed in order to measure the white reference tile and the intention is to enable the white reference tile to be positioned precisely in the measurement plane of the measurement optical path with the least possible structural complexity. When the white reference tile is in the parked position outside of the measurement optical path, it should not interfere with the normal operating mode of the device. Furthermore, the white reference tile should be protected from dirt and finally, positioning of the white reference tile in the measurement optical path and in the parked position outside of the measurement optical path should be as simple and ergonomic as possible.

This underlying objective of the invention is achieved by means of a hand-held light measuring device with a device housing, which has a bottom face incorporating a measuring window through which a measurement optical path extends so that a measurement object can be measured when the device housing is positioned with its bottom face on the measurement object, and with an integrated, displaceably mounted white reference tile which can be moved into the measurement optical path and moved back out of it again, characterized in that the white reference tile is disposed in an end region of an oblong support plate on its side directed towards the housing interior, which support plate is mounted so that it can be moved backwards and forwards between a parked position and an operating position, and the support plate terminates the device housing at its bottom face and is recessed into the device housing in the parked position, and the support plate is lifted out from the bottom face of the device housing and moved in the longitudinal direction and covers the measuring window by means of the end region incorporating the white reference tile to in the operating position.

In keeping with the thinking behind the invention, the white reference tile is disposed in an end region of an oblong support plate on its side directed towards the housing interior. The support plate is mounted so that it can be moved backwards and forwards between a parked position and an operating position and in the parked position, it terminates the device housing at its bottom face and is recessed into the device housing. In the operating position, the support plate is lifted out of the bottom face of the device housing and moved in the longitudinal direction and covers the measuring window by means of the end region incorporating the white reference tile. As a result of these features, the white reference tile is protected from dirt and the components of the measuring device disposed behind the measuring window can be easily protected from dirt in the operating position.

In one advantageous embodiment, the movement (kinematics) of the support plate and white reference tile disposed on it is effected by means of a combination of a rocker guide and pivot link. One the one hand, the support plate is mounted so that it can slide by means of a rocker guide disposed in the device housing in the end region remote from the white reference tile. On the other hand, the support plate is pivotably mounted on at least one pivot lever, which is in turn mounted so that it can pivot in the device housing. This combination is particularly practical and simple from a structural point of view. The support plate is advantageously suspended on a spring anchored in the device housing, which holds the support plate firmly in both its parked position and its operating position by a biasing action.

Based on another important aspect of the invention, it is of particular advantage if the pivot lever and spring are disposed so that their points of attack on the support plate are selected so that the spring is tensed more tightly during the movement of the support plate between the parked position and operating position and vice versa than when in the parked position and operating position and the spring automatically pulls the spring into the parked position or operating position and holds the support plate there by a biasing action having overshot the state of tightest tensing.

In one particularly advantageous embodiment of the invention, the white reference tile is mounted on the support plate so that it can be tilted in a sliding action on all sides. This offers a simple way of compensating for deviations in parallel positioning when moving the white reference tile into the operating position.

It is of particularly practical advantage if the white reference tile has a tile base part and a tile support part mounted on the support plate, which bears a tile film and is preferably disposed in the tile base part so that it can be tilted in a sliding action by means of complementary spherical surfaces. This results in a particularly simple way of imparting a tilting action to the white reference tile.

BRIEF DESCRIPTION OF THE DRAWINGS

An example of an embodiment of the hand-held light measuring device proposed by the invention will be described in more detail below with reference to the drawings. Of the drawings.

EXEMPLARY EMBODIMENTS OF THE PRESENT INVENTION

Figure 4:
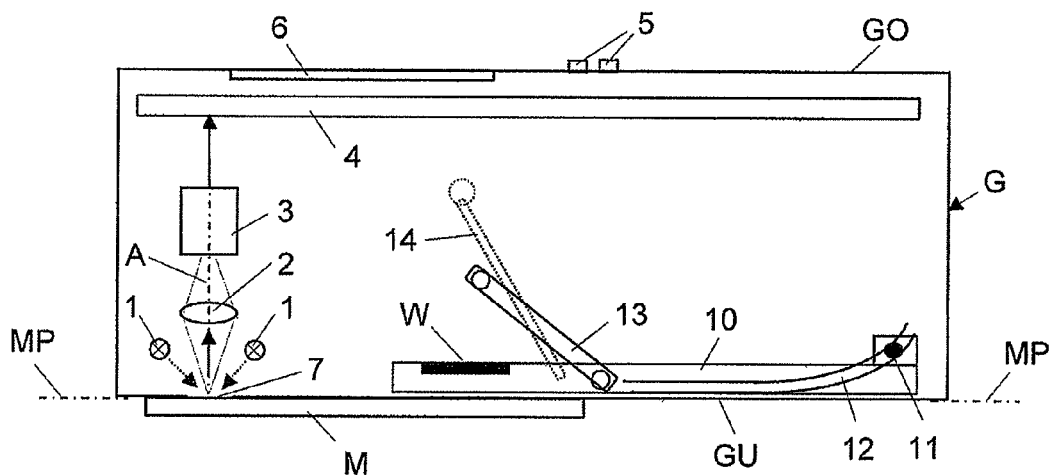

The illustrated hand-held light measuring device proposed by the invention comprises an essentially square housing G with rounded edges, in or on which all the functional components are accommodated. As may be seen in particular from FIGS. 4-6, these are a lighting arrangement 1, a measurement light pick-up arrangement 2, a photo-electric converter arrangement 3 and an evaluation and control electronic system 4. Disposed on the top face GO of the housing G (FIG. 1) are control keys 5 and a display device 6 (FIG. 4). Disposed on the bottom face GU of the housing G is a measuring window 7.

The lighting arrangement 1 comprises one or more light sources, which apply white or colored light to the measurement object M through the measuring window 7, usually at a normalized angle of incidence of 45°+−5°, for example. The measurement light pick-up arrangement 2 detects the measurement light reflected back from the measurement object, likewise through the measuring window 7, at a normalized range of measurement angles of 0°+−5°, for example, and forwards it to the converter arrangement 3. Depending on the configuration of the measuring device, the converter arrangement breaks down the measurement light forwarded to it into a greater or lesser number of wavelength ranges and converts either the total measurement, not broken down, or the individual light elements into corresponding electric, usually digital, signals. The latter are then evaluated by the evaluation and control electronic system 4 and prepared to obtain the measurement values of interest. The optical axis of the measurement light pick-up arrangement 2 is denoted by A (FIG. 4).

In a preferred example of an embodiment, the measurement object may be illuminated by several light sources, in particular light-emitting diodes, of different colors, in which case an imaging sensor is used as the converter arrangement. In the case of a light measuring device equipped with such an imaging sensor, the white reference tile is also used in particular for balancing the white of all the image pixels, i.e. eliminating any lack of homogeneity in the illumination, optical system and sensor.

In order to measure a measurement object M, the light measuring device is placed with its bottom face on the latter so that the measuring window 7 is positioned as centrally as possible, i.e. with the optical axis of the measurement optical path at the center of the measurement point of the measurement object of interest. The surface of the measurement object M is thus disposed in the measurement plane defined by the bottom face GU of the housing G, denoted by MP in FIGS. 4-6. A measurement operation is then initiated, for example by means of one of the control keys 5.

So far, the light measuring device described above corresponds fully and in all aspects to the known devices in terms of design and operation and the skilled person requires no further explanation.

Figure 5:
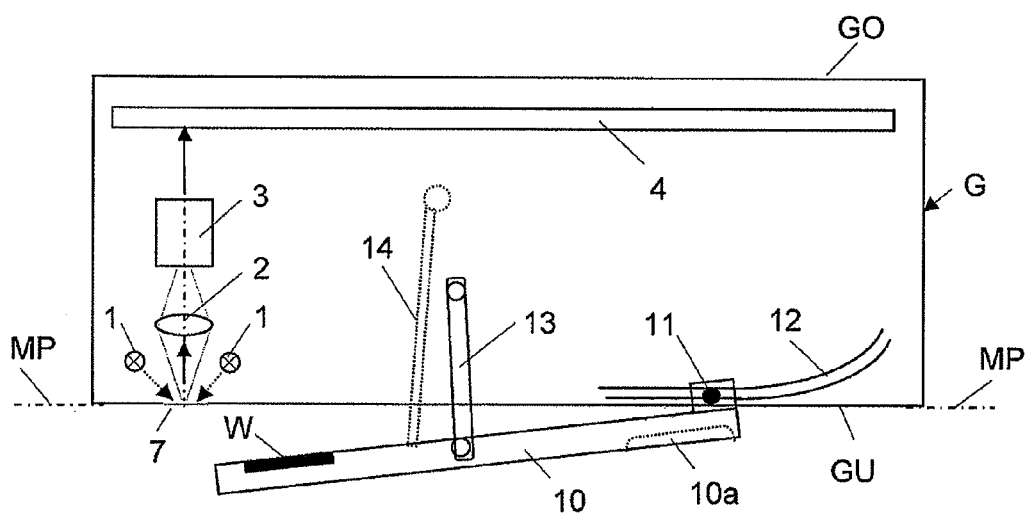
Figure 6:
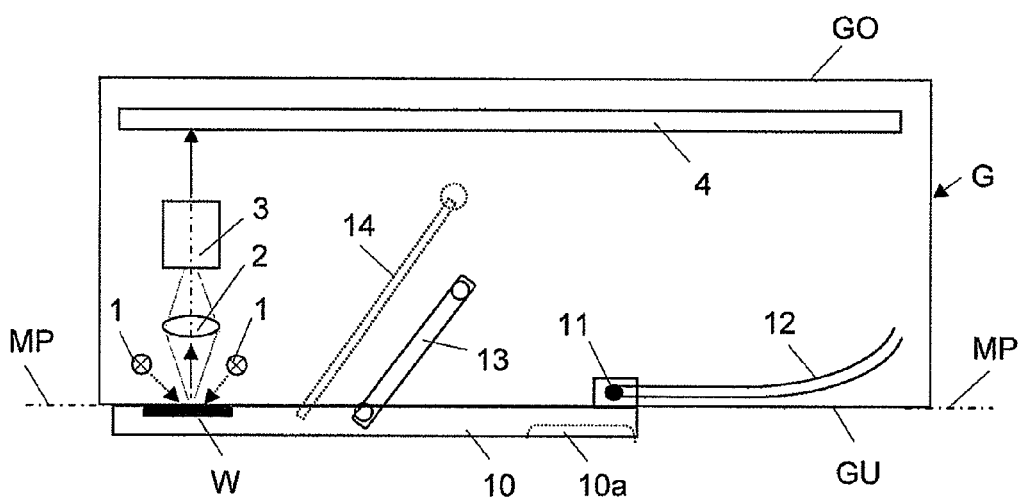

The most important difference which the light measuring device proposed by the invention has over devices known from the prior art is the design and disposition of the integrated white reference tile used to calibrate the device, which is denoted by W in FIGS. 4-6. By white reference tile within the meaning of this invention is meant not only a tile in the narrower sense but basically any type of physical color reference irrespective of its physical embodiment and, depending on the measuring device, this need not necessarily be white within the narrower sense and it must merely have an appropriately defined color with a sufficient long-term stability.

As proposed by the invention, the white reference tile W is disposed close to one end of an oblong support plate 10 on its inner face. The support plate 10 terminates the device housing G at its bottom face GU. By means of rocker guides 11 provided laterally at the other end of the support plate 10, formed by the ends of a round bar 11a (FIG. 7), the support plate 10 is guided as it slides in two laterally disposed guide rockers 12 lying opposite one another in the device housing G. The support plate 10 is also linked more or less centrally to two oppositely lying pivot levers 13 in the device housing G so that it can pivot. A spring 14 is attached to the support plate 10 by its one end and is anchored to the device housing by its other end. The spring 14 is preferably provided in the form of a torsion spring, although for the sake of simplicity it is illustrated in the form of a tension spring. In its end portion lying opposite the white reference tile W, the support plate 10 is provided with a gripping indentation 10a on its external face.

The support plate 10, and with it the white reference tile W, can be moved between a parked position and an operating position and is held sufficiently firmly in these two positions by the spring 14. The parked position is illustrated in FIG. 4 and the operating position in FIG. 6. FIG. 5 shows the support plate in an intermediate position. The combination of rocker guides and pivot links provides the kinematics for the movement.

Figure 1:
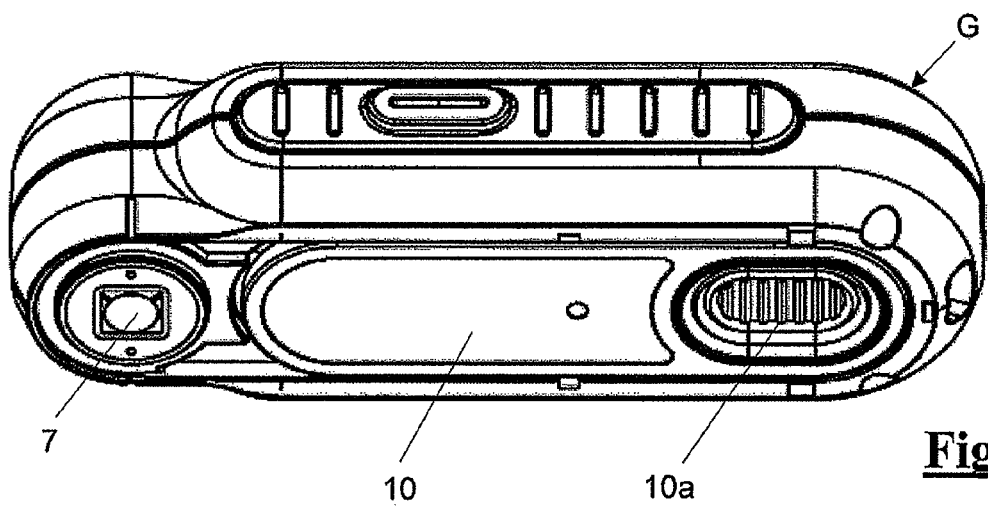
FIGS. 1-3 each illustrate a view of exemplary hand-held light measuring devices according to the present invention seen from an angle with its white reference tile in three different positions, FIGS. 4-6 each illustrate a schematic longitudinal section through the hand-held light measuring device with the white reference tile in the positions shown in FIGS. 1-3.

In the parked position illustrated in FIGS. 1 and 4, the support plate 10 is recessed into the device housing G and is disposed above the measurement plane MP. The white reference tile W is disposed completely inside the device housing and is therefore protected from dirt or access by the device user. The measuring window 7 is open when the support plate is in the parked position.

Figure 2:
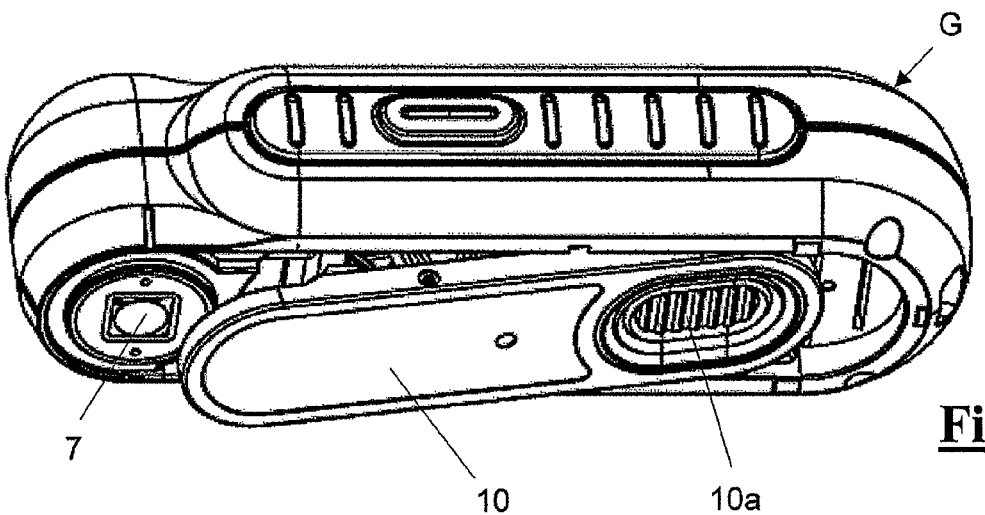
Figure 3:
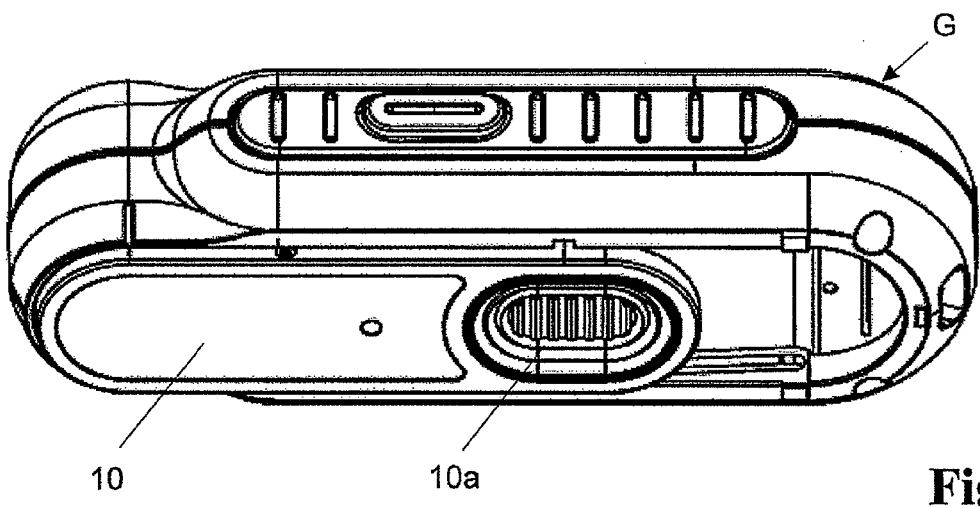

When the support plate 10 is moved in the direction towards the measuring window, the support plate is firstly lifted by its front end portion supporting the white reference tile and then as whole against the force of the spring 14 out from the bottom face GU of the device housing G (FIGS. 2 and 5). Finally, the support plate 10 reaches its operating position (FIGS. 3 and 6) in which its front end portion closes the measuring window 7 and the white reference tile W lies in the measurement optical path.

The support plate 10 now lies parallel with the device bottom face GU below the measurement plane MP and the surface of the white reference tile W is disposed exactly in the measurement plane MP and can now be measured for calibration purposes. When the support plate 10 is pushed back in the direction away from the measuring window 7, the support plate 10, and hence also the white reference tile W, is moved back into the parked position.

Due to the disposition of the pivot lever 13 and spring 14 and the points at which they act on the support plate, the spring 14 is initially tensed as the support plate 10 is moved from the parked position into the operating position and then slightly relaxed again. The same happens during the movement back into the parked position. This results in a sort of knee lever action due to which the spring 14 pulls the support plate 10 into one or the other of the two end positions and holds it there once it has passed the state of strongest tensing (dead center).

In the operating position, the support plate 10 covers the measuring window 7 and thus protects the components lying behind it from dirt. This is of advantage when it comes to storing the device.

In terms of complexity, only a very simple system is needed for the kinematics of the support plate 10 and white reference tile W and the support plate 10 and white reference tile W can be moved easily and comfortably.

Figure 7:
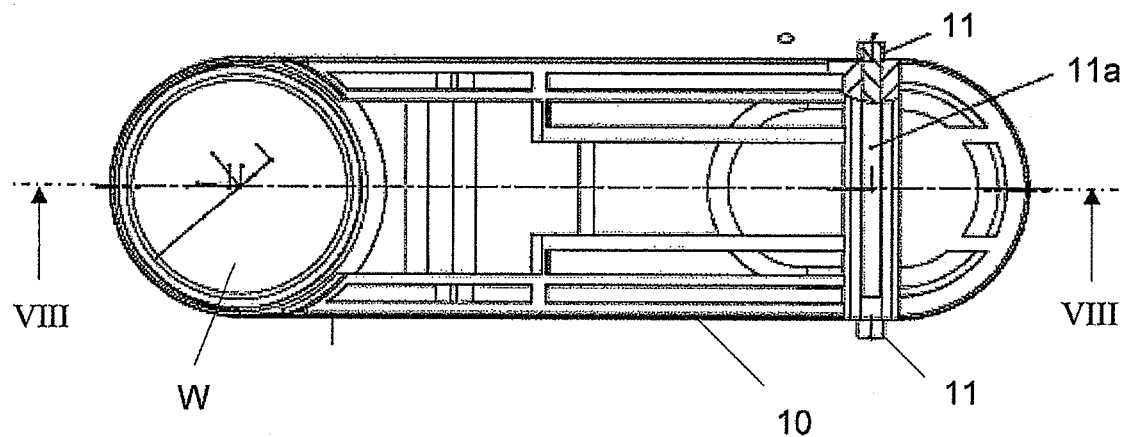
FIG. 7 is a view from inside and above showing a support plate serving as a mount for the white reference tile.
Figure 8:
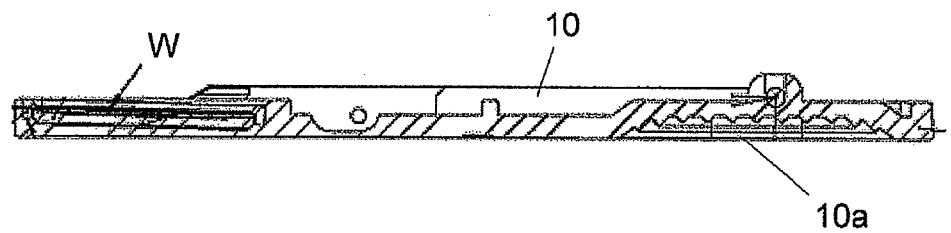
FIG. 8 is a section through the support plate along line VIII-VIII indicated in FIG. 7.
Figure 9:
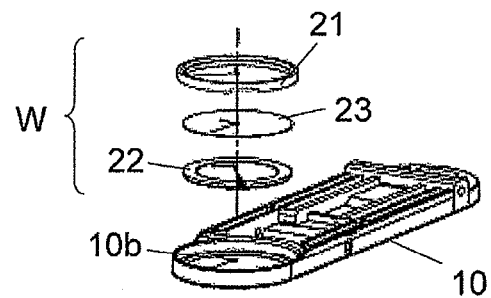
FIG. 9 is an exploded diagram of the support plate and white reference tile.

FIGS. 7-9 illustrate a particularly advantageous embodiment of the support plate 10 and more especially the white reference tile W. As may be seen from FIG. 9 in particular, the support plate 10 is provided with a mounting indentation 10b on the internal face at its end lying opposite the gripping indentation 10a, in which the white reference tile W is fixedly mounted. The white reference tile W physically comprises three parts, namely a tile base part 21, a tile support part 22 and a tile film 23 constituting the actual white reference. The tile base part 21 is placed in the mounting indentation 10b and secured. The tile support part 22 is mounted in the tile base part 21 so that it is able to tilt to a limited degree on all sides and bears the tile film 23 on its surface. The tile support part 22 is able to tilt in and relative to the tile base part 21 due to the fact that the tile base part 21 and tile support part 22 are provided with complementary spherical surfaces 21a and 22a and lie one against the other so that they are able to slide by means of these spherical surfaces.

Figure 10A:
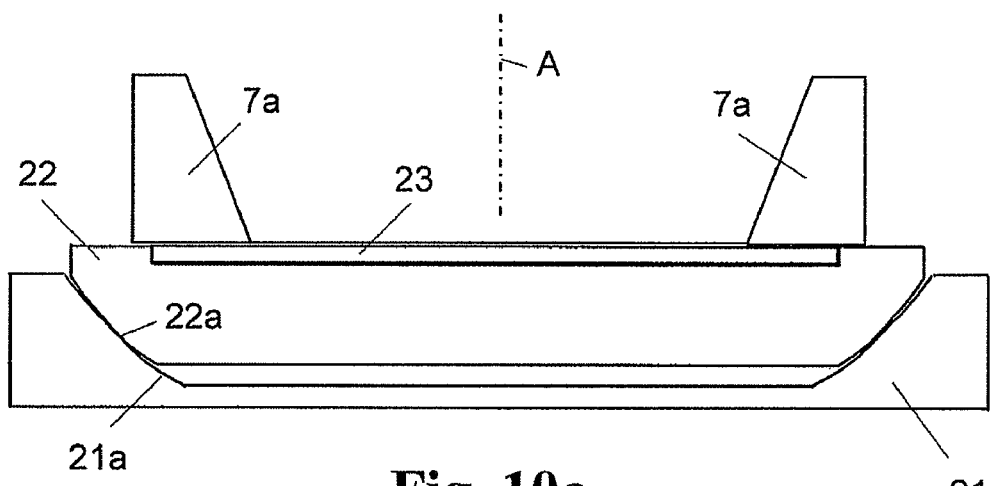
FIG. 10a-c are diagrams illustrating how the slide mounting of the white reference tile on the support plate operates.

In order to take a correct and precise measurement of the white reference tile W, it is necessary for the measurement light pick-up arrangement 2 to be oriented precisely in the measurement plane of the measuring window 7 and perpendicular to the optical axis A during the measuring operation. Ideally, the individual parts of the white reference tile W then assume the positions illustrated in FIG. 10a. The measurement aperture is denoted by reference 7a.

Figure 10B:
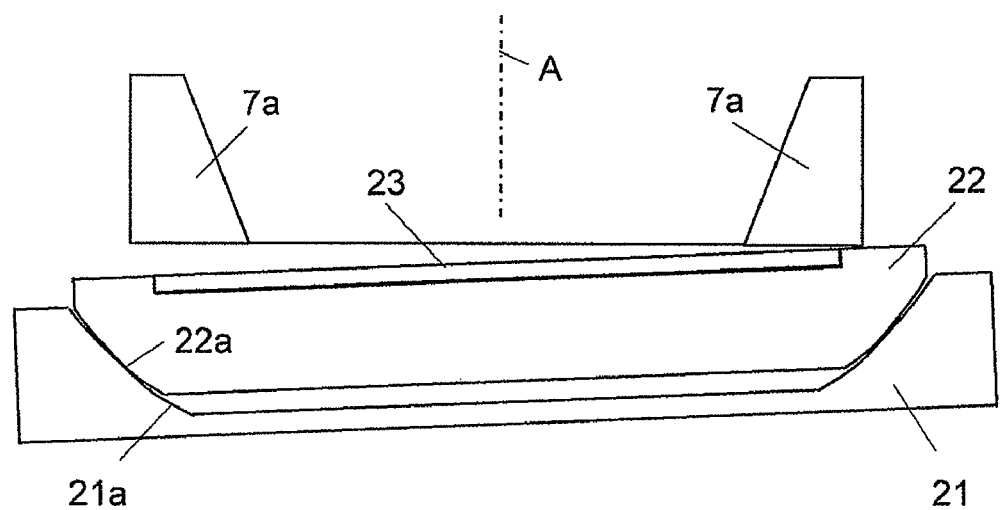
Figure 10C:
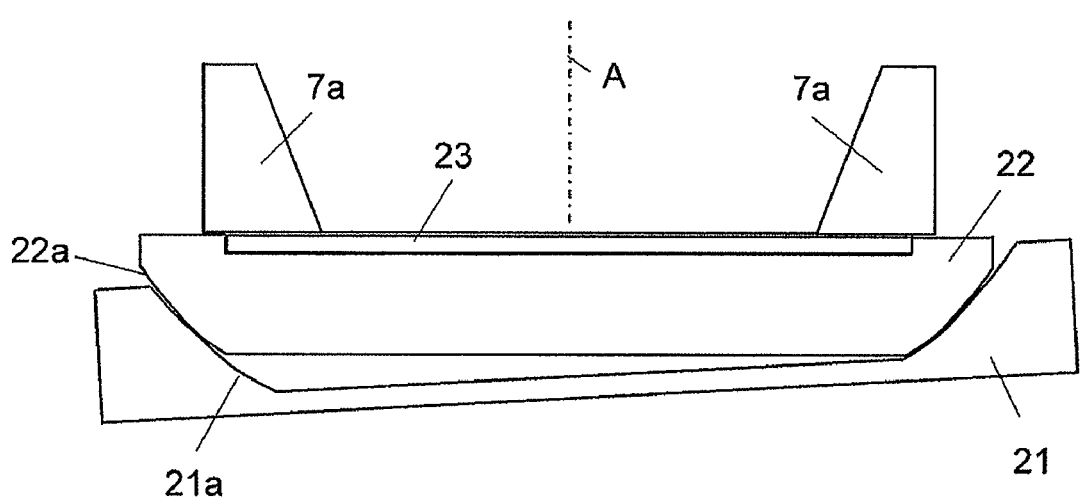

If, for some reason, the support plate 10 is not positioned exactly parallel with the housing bottom face and measurement plane, the white reference tile W would then normally sit at an angle with respect to the measurement plane in front of the measurement aperture 7a, as illustrated in FIG. 10b, for example. Due to the mounting of the tile support part 22 in the tile base part 21 proposed by the invention which enables it to tilt on all sides, however, the surface of the white reference tile W is automatically oriented in the correct position, ruling out errors due to non-parallel positioning. The support plate 10 and the white reference tile W mounted on it merely have to be pushed lightly towards the measurement aperture 7a. This is illustrated in FIG. 10c.

The design of the white reference tile W and its kinematic arrangement are suitable for any type of hand-held light measuring device. Accordingly, the invention is not restricted to light measuring devices in the narrower since and in particular includes every type of color measuring device or densitometer or similar.

The invention claimed is:

1. A hand-held light measuring device comprising:
 a. a device housing with a bottom face incorporating a measuring window through which a measurement optical path extends so that a measurement object can be measured when the device housing is positioned with its bottom face on the measurement object, and
 b. an integrated, displaceably mounted white reference tile which can be moved into the measurement optical path and moved back out of it again,
  wherein the white reference tile is disposed in an end region of an oblong support plate on its side directed towards the housing interior, which support plate is mounted so that it can be moved backwards and forwards between a parked position and an operating position,
  wherein the support plate terminates the device housing at its bottom face and is recessed into the device housing in the parked position, and
  wherein the support plate is adapted to be lifted out of the bottom face of the device housing and moved in the longitudinal direction so as to cover the measuring window with the end region incorporating the white reference tile in the operating position.

2. The hand-held light measuring device according to claim 1, wherein the support plate is mounted so that it is able to slide with an end region facing away from the white reference tile in guide rockers provided in the device housing.

3. The hand-held light measuring device according to claim 2, wherein the support plate is linked to at least one pivot lever which is in turn mounted in the device housing so that it is able to pivot.

4. The hand-held light measuring device according to claim 3, wherein the support plate is suspended on a spring anchored in the device housing.

5. The hand-held light measuring device according to claim 4, wherein the spring firmly retains the support plate in both its parked position and its operating position by a biasing action.

6. The hand-held light measuring device according to claim 5, wherein the pivot lever and spring are disposed in such a way and their points of attack on the support plate selected so that the spring is more tightly tensed during the movement of the support plate between the parked position and the operating position and vice versa than it is in the parked position and operating position, and the spring automatically pulls the support plate into the parked position or operating position and holds it there by a biasing action having passed the state of tightest tensing.

7. The hand-held light measuring device according to claim 1, wherein the white reference tile is mounted on the support plate so that it is able to tilt in a sliding action on all sides.

8. The hand-held light measuring device according to claim 7, wherein the white reference tile includes a tile base part on the support plate and a tile support part bearing a tile film and is disposed in the tile base part so that it can tilt in a sliding action by means of complementary spherical surfaces.

9. The hand-held light measuring device according to claim 1, wherein the support plate is provided with a gripping indentation.

10. The hand-held light measuring device according to claim 1, further comprising a lighting arrangement for illuminating a measurement point on the measurement object, a pick-up arrangement for detecting the measurement light reflected back from the measurement object, a converter arrangement for converting the measurement light into corresponding electric signals, and an evaluation and control electronic system for evaluating the electric signals and controlling the operating sequences of the measuring device.

* * * * *